United States Patent [19]
Knoth

[11] Patent Number: 5,472,412
[45] Date of Patent: Dec. 5, 1995

[54] LIMB BRACE WITH ADJUSTABLE HYDRAULIC RESISTANCE UNIT

[75] Inventor: Donald E. Knoth, Dayton, Ohio

[73] Assignee: Mauch Laboratories, Inc., Dayton, Ohio

[21] Appl. No.: 222,878

[22] Filed: Apr. 5, 1994

[51] Int. Cl.[6] ............................................. A61F 5/00
[52] U.S. Cl. .................... 602/26; 602/16; 602/20; 602/23; 602/27; 428/111; 428/112
[58] Field of Search ................... 602/16, 20, 23, 602/26; 623/46; 482/111, 112, 113

[56] References Cited

U.S. PATENT DOCUMENTS

| | | | |
|---|---|---|---|
| 2,859,451 | 11/1958 | Mauch | 602/26 X |
| 3,316,558 | 5/1967 | Mortensen | 602/26 X |
| 3,799,159 | 3/1974 | Scott | 602/26 X |
| 3,976,057 | 8/1976 | Barclay | 601/34 |
| 4,801,138 | 1/1989 | Airy et al. | 602/16 |
| 5,052,379 | 10/1991 | Airy et al. | |
| 5,103,811 | 4/1992 | Crupi, Jr. | 602/26 X |

Primary Examiner—Linda C. M. Dvorak
Assistant Examiner—Kim M. Lee
Attorney, Agent, or Firm—Jacox, Meckstroth & Jenkins

[57] ABSTRACT

An articulated knee brace includes a pair of arms pivotally connected by corresponding pivot pins and gear segments supported by a set of hub plates having holes for receiving adjustable stop pins. The arms are attached by flexible and releasable bands to a person's limb on opposite sides of a joint, and one of the arms carries an adjustable hydraulic control unit. The unit includes a tubular housing enclosing a pair of axially spaced pistons rigidly connected by a shaft, and a curved link member connects the pistons to the hub plates eccentrically of the pivot axes. A set of manually rotatable valves are supported by the housing between the pistons and variably control the flow of hydraulic fluid through the valves and between the piston chambers in response to pivoting of the arms for selectively and independently adjusting the resistance to flexion and extension of the brace and limb.

14 Claims, 4 Drawing Sheets

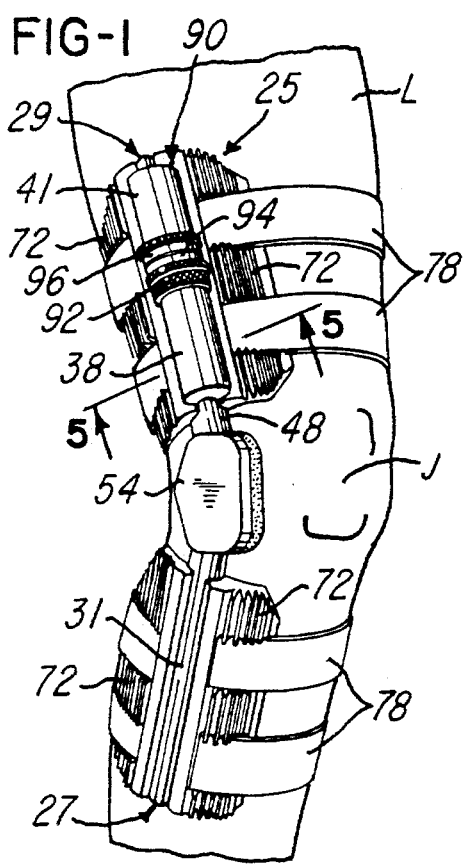
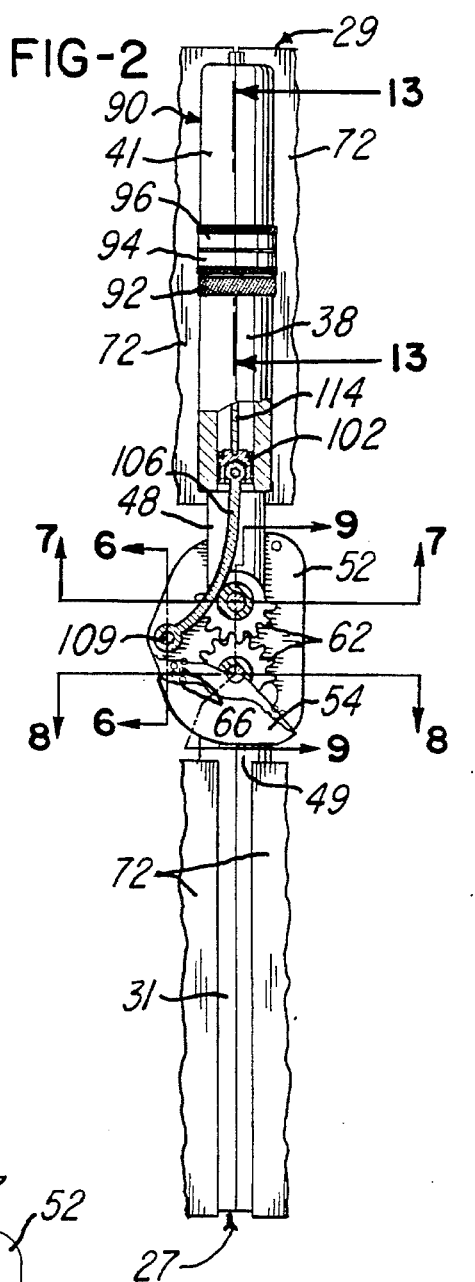
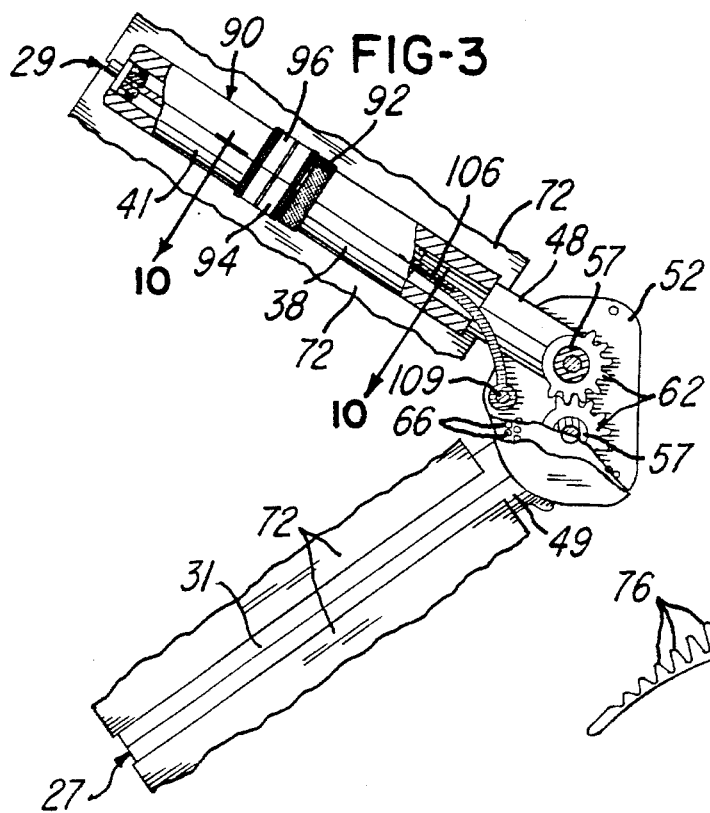
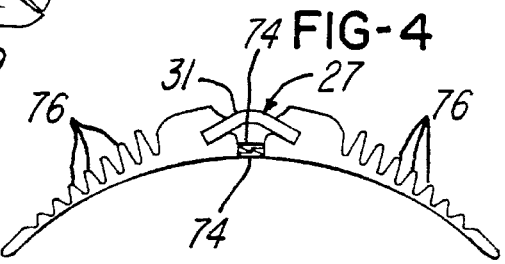

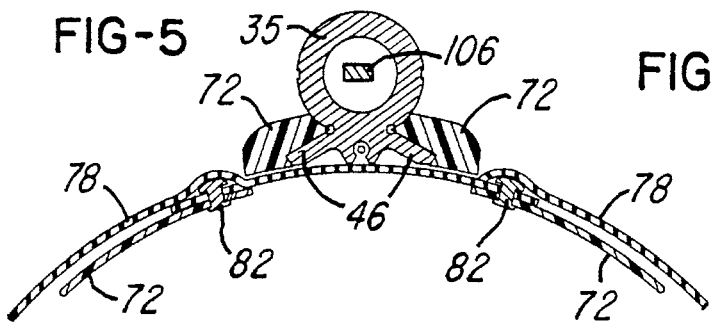
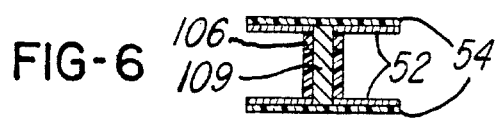
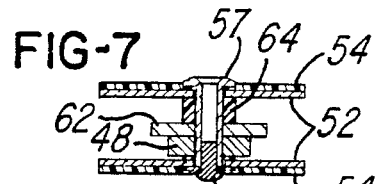
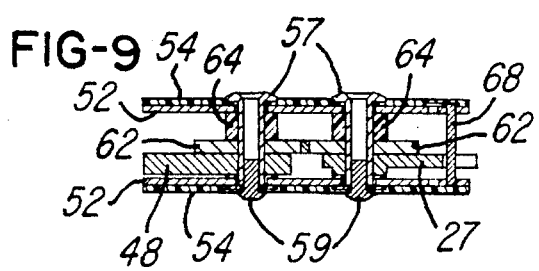
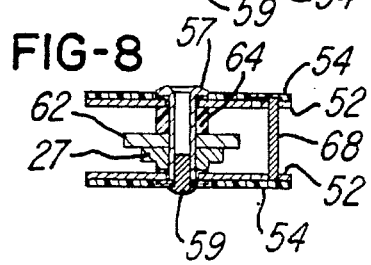
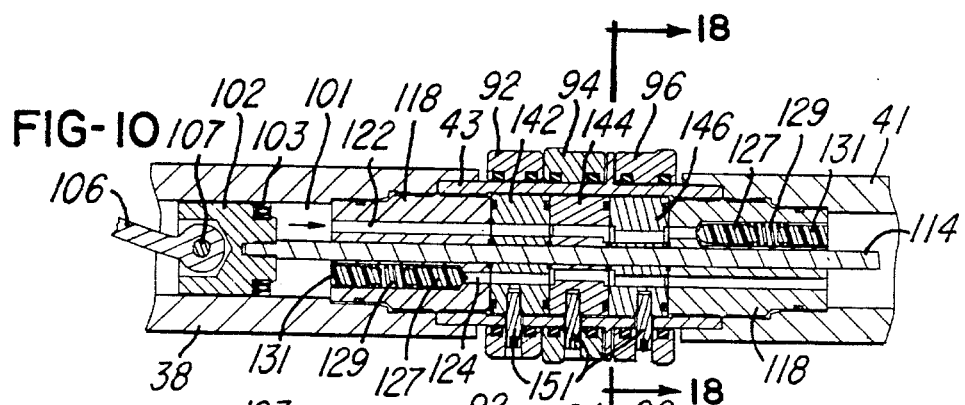
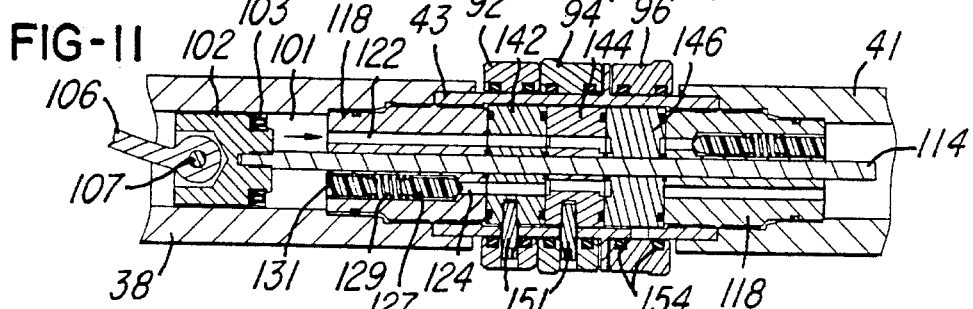
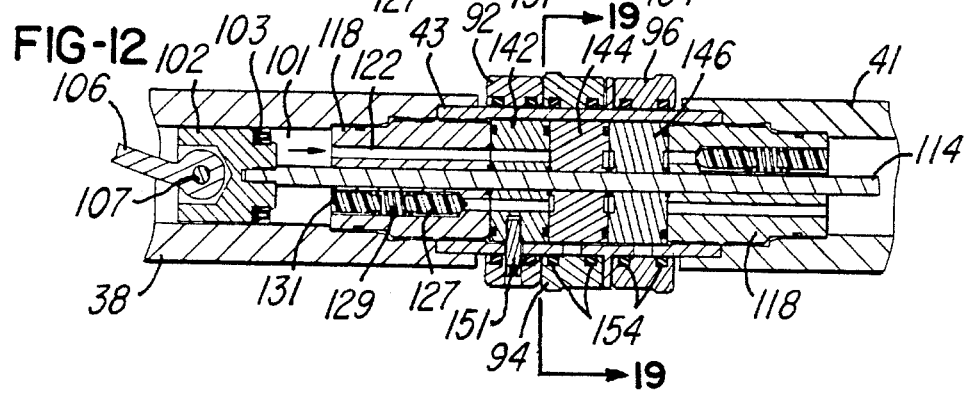

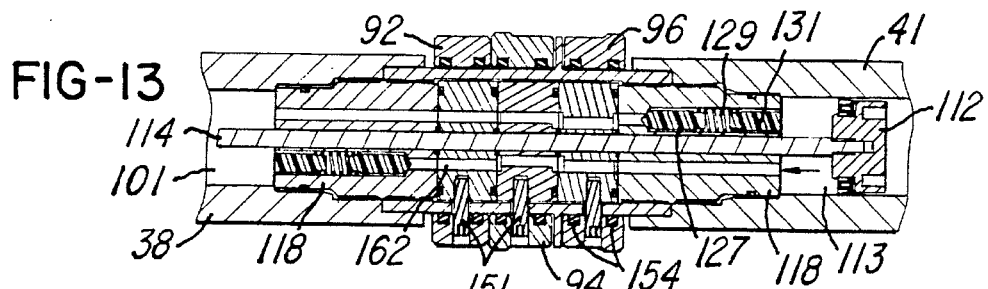
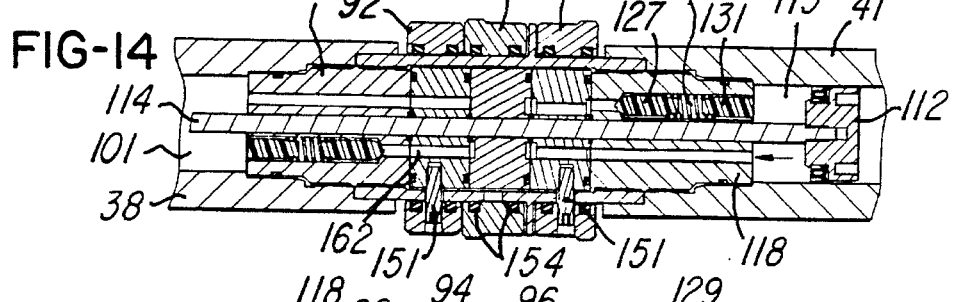
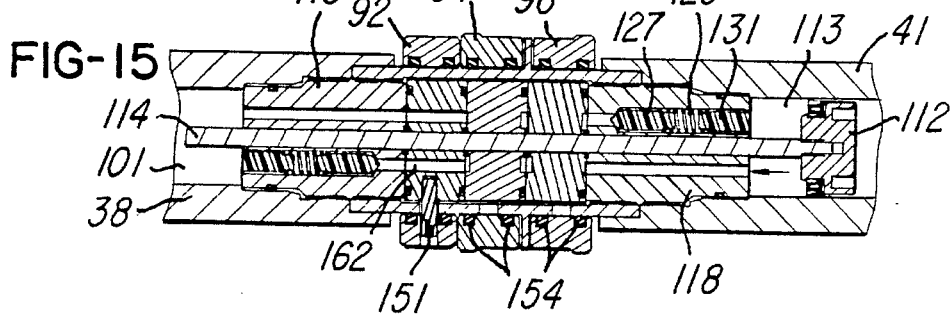
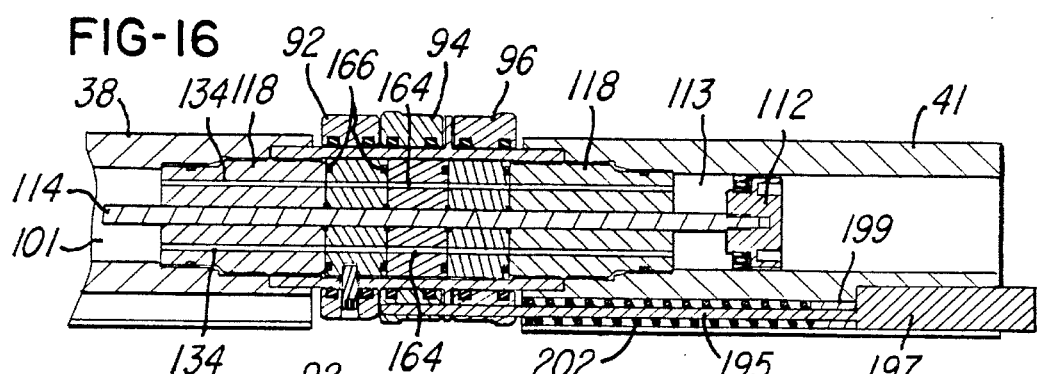
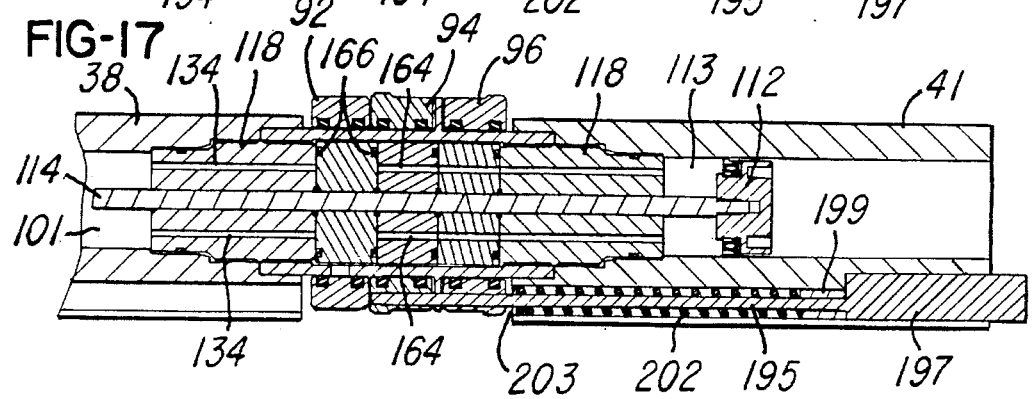

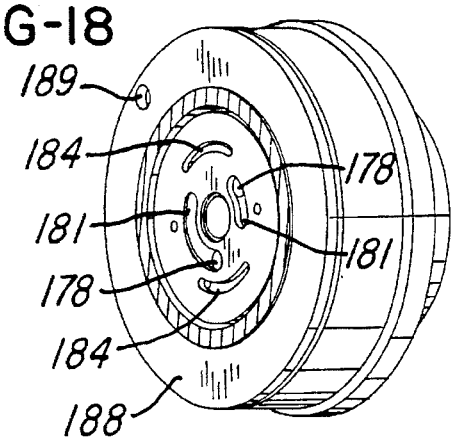
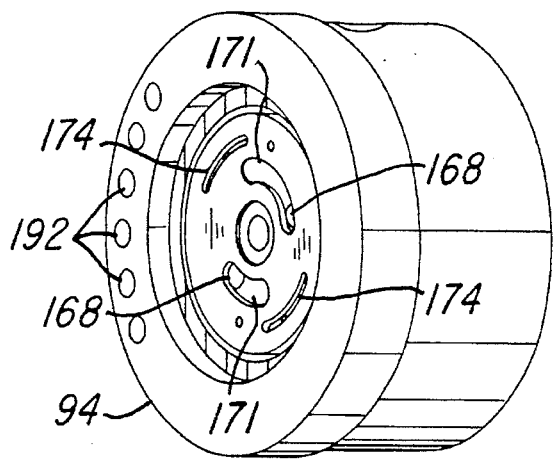

LIMB BRACE WITH ADJUSTABLE HYDRAULIC RESISTANCE UNIT

BACKGROUND OF THE INVENTION

The present invention relates to articulated braces of the general type disclosed in U.S. Pat. No. 5,052,379 and which are used on a person's arm or leg to assist flexion and extension of the arm or leg during rehabilitation or health training. Commonly, such a brace includes two pairs of arms which are pivotally connected by corresponding hub components, and each pair of arms is attached by releasable straps to a person's arm or leg with the pivot axis generally aligned with the pivot axis of a joint within the arm or leg. Usually, the hub components of the brace are provided with adjustable or repositionable stop pins which limit the angle of pivotal movement of the brace and the corresponding flexion of the arm or leg.

As disclosed in the above patent, it is sometimes desirable to provide the brace with a resistance to pivotal movement to provide for exercising the arm or leg against a preselected torque or resistance. As disclosed in the above patent in connection with FIGS. 5 and 6, the resistance may be provided by the shear resistance of a viscous fluid which resists rotation of a rotor in opposite directions within a housing. The resistance is varied by changing the viscosity of the fluid or by changing the clearance space between the rotor and the surrounding housing.

It has been found desirable for an articulated brace to provide for conveniently selecting between no resistance and a predetermined resistance depending upon the purpose for which the brace is used. It has also been found desirable for the brace to provide for conveniently adjusting the resistance to flexion of the brace and the resistance to extension of the brace. Furthermore, it is desirable for the brace to provide for selecting or varying the resistance to flexion or extension and independently of each other.

SUMMARY OF THE INVENTION

The present invention is directed to an improved limb brace incorporating an adjustable resistance unit which provides all of the desirable features mentioned above. That is, the limb brace of the invention provides for conveniently selecting between no resistance and a resistance, for adjusting the resistance against flexion of the brace and for independently adjusting the resistance to extension of the brace. In addition, the brace of the invention provides for conveniently selecting the resistance between a low resistance and a maximum resistance without removing the brace from the limb.

In accordance with one embodiment of the invention, the above features are provided by a brace which includes a pair of arms pivotally connected by gear segments and cross shafts confined between a set of hub plates. The hub plates have a series of aligned holes for adjustably receiving cross pins which limit the simultaneous movement of the arms relative to the hub plates. The arms are releasably attached by flexible bands to a person's limb on opposite sides of a body joint, and one of the arms carries an adjustable hydraulic control unit. The control unit includes a tubular housing defining chambers which receive a pair of axially spaced pistons rigidly connected by a shaft, and a curved link member connects the pistons to the hub plates eccentrically of the pivot axes for the arms. A set of disk-like valve members are rotatably supported by the housing between the piston chambers and adjustably control the flow of hydraulic fluid through the valves when the pistons move in response to flexing of the brace. The valve members provide for selectively and independently adjusting the resistance to flexion and extension of the brace arms.

Other features and advantages of the invent ion will be apparent from the following description, the accompanying drawings and the appended claims.

BRIEF DESCRIPTION OF THE DRAWINGS

FIG. 1 illustrates a perspective view of one side of an articulated brace constructed in accordance with the invention and shown attached to a leg at the knee joint.

FIG. 2 is an elevational view of the brace shown in FIG. 1 when the brace is in an extension position, and with portions broken away to show internal construction;

FIG. 3 is a view similar to FIG. 2 and showing the brace in a fully flexed position;

FIG. 4 is a lower end view of the brace shown in FIG. 1;

FIG. 5 is an enlarged fragmentary section taken generally on the line 5—5 of FIG. 1;

FIGS. 6–9 are fragmentary sections taken generally on the lines 6—6, 7—7, 8—8, and 9—9, of FIG. 2;

FIG. 10 is a fragmentary section of the hydraulic control unit shown in FIG. 1 and taken generally on the line 10—10 of FIG. 3 during flexion of the brace;

FIGS. 11 and 12 are fragmentary sections similar to FIG. 10 and showing different positions of internal control valves;

FIG. 13 is a fragmentary section similar to FIG. 10 and taken generally on the line 13—13 of FIG. 2 during extension of the brace;

FIGS. 14–17 are views similar to FIG. 13 and showing different positions of the internal control valves;

FIG. 18 is a perspective view of the extension control valve, taken generally on the line 18—18 of FIG. 10; and FIG. 19 is a perspective view of the flexion control valve, taken generally on the line 19—19 of FIG. 12.

DESCRIPTION OF THE PREFERRED EMBODIMENT

FIG. 1 illustrates one side of an articulated brace 25 which is attached to a leg L and extends across the knee joint J. The other side of the brace is not shown, but the brace 25 is generally similar to a knee brace manufactured by Smith & Nephew DonJoy Inc. of Carlsbad, Calif. and sold under the trademark DONJOY. Each side of the brace 25 includes a set of elongated bars or arms 27 and 29, and the arm 27 is formed from a flat strip of metal or aluminum with an outer portion 31 (FIG. 4) bent along its length to have a V-shaped cross-sectional configuration. The arm 29 is formed from a tubular extrusion which is machined to form a tubular housing 35 (FIG. 5) including axially spaced housing sections 38 and 41 rigidly connected by a metal tube 43 (FIG. 10). At the base of each housing section 38 and 41, the tubular extrusion has a pair of diverging flanges 46 (FIG. 5) which are machined away to form a flat inner end portion 48 (FIG. 2).

A flat inner end portion 49 of the arm 27 and the flat inner end portion 48 of the housing 35 project inwardly between a pair of metal hub plates 52 (FIG. 9) each of which is covered by a plastic outer cover sheet 54. As shown in FIG. 9, the inner end portions 48 and 49 of the arms 27 and 29 are pivotally supported by corresponding tubular cross pins or shafts 57 retained by screws 59 which also retain the outer cover sheet 54. An arcuate gear segment or section 62 is rigidly secured or staked to each of the inner end portions 48 and 49 of the arms, and the gear segments 62 mesh, as shown in FIG. 2, to provide for simultaneous pivotal movement of the arms 27 and 29. A tubular spacer collar 64 of rigid plastics material is mounted on each of the arm support shafts 57 to prevent the arms from shifting axially on the shafts.

The hub plates 52 have a series or arcuately spaced aligned pairs of holes 66 which are partially shown in FIG. 2 for selectively receiving adjustable cross stop pins 68 (FIGS. 8 and 9) for limiting the angular movement of the arms 27 and 29 relative to the hub plates 52. After the screws 59 and outer cover sheet 54 are removed, each stop pin 68 may be selectively positioned in a different set of aligned holes 66 for limiting or changing the angle of movement of the arms.

Referring to FIGS. 1, 4 and 5, each of the arms 27 and 29 carries a pair of opposing molded flexible nylon pads 72 which receive the opposite edge portions of the arm 27 and the outer flange portion 31 of the arm 29. Each pair of opposing pads 72 are molded with inwardly projecting and overlapping hook portions 74 (FIG. 4) which interconnect the opposing pads together and retain the pads on the corresponding support arm. Each pair of pads 72 is molded with tapering parallel ribs 76 interrupted by a set of recesses through which extend a pair of flexible bands or straps 78. As shown in FIG. 5, the inner end portions of the straps 78 are notched, and interleaved portions of the straps extend under the tubular housing 35 and are secured to the pads 72 by a set of rivets 82. The outer end portions (not shown) of the flexible straps 78 are secured together by loop and hook fasteners (not shown) commonly known as VELCRO fasteners. When the straps 78 are pulled around the leg L, the tension in the straps 78 pulls the flexible pads 72 firmly onto the outer portion 31 of the arm 27 and the flange portions 46 of the housing 35 or arm 29, as shown in FIG. 5.

Referring to FIGS. 10–17, the tubular housing 35 forms part of a hydraulic resistance unit 90 (FIG. 1) which functions to resist the relative angular movement of the arms 27 and 29 in both directions. The arms move relative to the hub plates 52 and between an extension position (FIG. 2) and a flexion position (FIG. 3) as will be explained. The resistance to articulated movement of the brace may be selected between low resistance and maximum resistance, simply by selectively rotating a set of three control members or rings 92, 94 and 96. The ring 92 provides selection between no resistance and resistance and is thus an on/off control. The ring 94 provides for infinitely selecting the resistance to flexion of the brace, and the ring 96 provides for selecting the resistance to extension of the brace.

As shown in FIGS. 10–12, the housing section 38 defines a cylindrical chamber 101 and slidably supports a cylindrical piston 102 which carries a resilient sealing ring 103. The piston 102 is pivotally connected to one end of an arcuate link member 106 by a pivot pin 107, and the opposite end of the link member 106 is pivotally connected to the hub plates 52 (FIG. 3) by a cross pin 109. As shown in FIGS. 2 and 3, the eccentric connection of the pivot pin 109 relative to the axes of the pivot shafts or pins 57 causes the piston 102 to move axially within the housing chamber 101 in response to pivoting movement of the arms 27 and 29. Referring to FIG. 13, a second piston 112 is supported for axial movement within a cylindrical chamber 113 defined by the housing section 41 and also carries a sliding fluid-tight sealing ring 103. The pistons 102 and 112 are rigidly connected by a center rod or shaft 114 which has opposite end portions threaded into the pistons. Thus movement of the piston 102 within the chamber 101 is effective to move the piston 112 simultaneously within the chamber 113.

A valve body 118 is threaded into the inner end portion of each of the housing sections 38 and 41, and each valve body 118 defines a center bore for slidably receiving the piston connecting rod or shaft 114 and also defines a set of axially extending passages 122 and 124. A check valve member 127 is supported within an enlarged portion of the passage 124 of each body 118 and is urged to a normally closed position by a compression spring 129 extending from a plug 131 having peripherally spaced and axially extending channels. Each valve body 118 also defines a pair of axially extending passages 134 (FIG. 16), and all of the corresponding passages within the two valve bodies 118 are axially aligned.

A set of three cylindrical valve members 142, 144 and 146 (FIGS. 10–15) are supported for independent rotation within the cylinder 43 between the valve bodies 118. The valve members 142, 144 and 146 are connected to the surrounding corresponding control rings 92, 94 and 96, respectively, by radial pins 151 which project inwardly from the rings through corresponding arcuate slots within the tube 43. Each of the connecting pins 151 is threaded into its corresponding control ring, and a pair of resilient O rings 154 form rotary friction seals between each control ring and the support tube 43.

The valve member 142 has a pair of axially extending cylindrical passages 162 (FIG. 14) which align with the passages 122 and 124 within the valve bodies 118 when the valve member 142 and its control ring 92 are in their resistance "On" position. The valve member 142 also has a pair of passages 164 (FIG. 16) which align with the passages 134 within the valve bodies 118 when the valve member 142 is in its resistance "Off" position. The opposite radial end surfaces of the valve member 142 have annular grooves which carry resilient O-ring seals 166. The valve member 142 and its corresponding control ring 92 are rotatable as a unit between the "On" position (FIGS. 10–15) when resistance is on, and an "Off" position (FIG. 16) when resistance is off and hydraulic fluid within the chambers 101 and 113 is free to flow back and forth between the chambers and through the passages 164 within the valve member 142.

The resistance to flexion may be variably adjusted by rotating the middle control ring 94 and its corresponding valve member 144. As shown in FIGS. 10 and 19, the valve member 144 has a pair of axially extending passages 168, and the ends of the passages 168 adjacent the valve member 142 have corresponding arcuate tapered channels 171. The valve member 144 also has a pair of diametrically opposed and axially extending arcuate passages 174 which always align with the passages 134 within the valve bodies 118, as shown in FIG. 16. Similarly, the extension control valve member 146 (FIG. 18) has a pair of axially extending holes or passages 178, and the ends of the passages 178 adjacent the valve member 144 have corresponding arcuate tapered channels 181. A pair of axially extending arcuate passages 184 are adapted to align axially with the passages 174 within the valve member 144 and with the cylindrical passages 164 within the valve member 142, as shown in FIG. 16.

Referring to FIGS. 10–18, the housing connector tube 43 has an outwardly projecting radial flange 188 which has a single hole 189 (FIG. 18). Each of the control rings 94 and 96 has a plurality of circumferentially spaced and axially extending holes 192 (FIG. 19) each of which may be selectively and axially aligned with the hole 189. A lock pin 195 (FIGS. 16 and 17) is adapted to extend axially through one of the holes 192 in each of the control rings 94 and 96 and also through the single hole 189 within the flange 188 to prevent the control rings 94 and 96 and corresponding valve members 144 and 146 from rotating after they are adjustably positioned.

The lock pin 195 (FIGS. 16 & 17) extends within a bore within the housing section 41 and has an eccentrically positioned cylindrical head portion 197 which normally projects slightly from the housing section 41. A bushing 199 is pressed into the bore within the housing section 41 and supports the lock pin 195 for axial movement and for rotation. A compression spring 202 extends from the bushing 199 to a retaining ring 203 secured to the lock pin 195 and normally urges the lock pin to its locking position, as shown in FIGS. 16 and 17. When it is desired to release the control valves 144 and 146 for adjusting the resistance to flexion and/or extension, respectively, the pin 195 is retracted from the holes 189 and 192.

As mentioned above, the annular chambers 101 and 113 defined within the housing sections 38 and 41 between the pistons 102 and 112 and valve bodies 118 are filled with a hydraulic fluid such as a low viscous oil. As mentioned above, the fluid also fills all of the passages within the valve bodies 118 and valve members 142, 144 and 146. The control ring 92 and the corresponding valve member 142 are rotatable between two positions. In one position (FIG. 16), the oil is free to flow between the chambers 101 and 113 through the passages 134, 164, 174, 184 in response to movement of the pistons 102 and 112 within the chambers. In the other position (FIG. 17), the oil is forced to flow through the passage 124 within one of the valve bodies 118 and past the corresponding check valve member 127 within the other valve body 118, depending upon the direction of movement of the pistons. During flexion of the brace 25, oil is forced from the chamber 101 to the chamber 113 and through the ports 168 within the center valve member 144. As the valve member 144 is rotated by rotating its corresponding control ring 94, the restriction of the oil flow is changed by the tapered channels 171 (FIG. 19) so that the resistance to flexion may be controlled by adjustably rotating the control ring 94.

During extension of the brace 25, the oil transfers from the chamber 113 to the chamber 101 and through the passage 124 and past the check valve member 127 within the left valve body 118 shown in FIG. 10. By rotating the extension control ring 96 and the corresponding valve member 146, the oil flow is variably restricted by the tapered channels 181 (FIG. 18) within the face of the valve member 146 so that the restriction to extension is infinitely adjustable. After the flexion control ring 94 and the extension ring 96 are rotatably positioned to the desired resistance to flexion and the desired resistance to extension and while the lock pin 195 is retracted, the lock pin is then extended so that it extends through one of the holes 192 within the extension control ring 96, the hole 189 within the flange 188 and one of the holes 192 within the flexion control ring 94, as shown in FIGS. 16 and 17. This prevents rotation of the control rings 94 and 96 until the lock pin 195 is again retracted. In its retracted position, the lock pin may be rotated 180° so that the eccentric head portion 197 engages the end surface of the housing section 41 for holding the lock pin in its retracted position during adjustment of resistance for flexion and/or extension.

From the drawings and the above description, it is apparent that a brace constructed in accordance with the present invention, provides desirable features and advantages. As a primary feature, the hydraulic control unit 90 provides the brace 25 with independent adjustment for the resistance to flexion and the resistance to extension of the brace. By rotating the control ring 92, the unit also provides for selecting between resistance and no resistance. When resistance is selected, independent rotation of the control rings 94 and 96 provides for incrementally selecting the degree of resistance to flexion and/or the degree of resistance to extension.

The control unit 90 is also compact in construction and provides for convenient selection by the user of resistance or no resistance, simply by rotating the on/off control ring 92. This selection may be made by the user after the brace is installed and without removing the brace from the leg, and the resistance to flexion and/or extension may be conveniently adjusted simply by retracting the lock pin 195 and independently adjusting the control rings 94 and/or 96. The arrangement of the arcuate mounting pads 72 and the interleaving connection of the attachment bands or straps 78 to the pads, as shown in FIG. 5, provide the advantage of the pads 72 gripping the brace arms 27 and 29 with increasing force as the attachment straps 78 are tightened.

While the form of brace herein described constitutes a preferred embodiment of the invention, it is to be understood that the invention is not limited to this precise form of brace, and that changes may be made therein without departing from the scope and spirit of the invention as defined in the appended claims.

The invention having thus been described, the following is claimed:

1. An articulated limb resistance device comprising a hub member, a set of arms projecting outwardly from said hub member, pivot means connecting said arms to said hub member for pivotal movement of said arms relative to each other, a hydraulic resistance unit including a tubular housing mounted on one of said arms, piston means supported within said housing for axial movement, means including a link member connecting said piston means to said hub member eccentrically of the pivot axis of said one arm and means to move said piston means within said housing in response to pivoting said arms, and means including an adjustable control valve supported by said housing for controlling the displacement of hydraulic fluid within said housing in response to movement of said piston means for adjustably selecting the resistance to pivotal movement of said arms.

2. A device as defined in claim 1 wherein said piston means comprise a set of axially spaced pistons supported within said housing for axial movement, and said control valve is positioned within said housing between said pistons to restrict the displacement of fluid within said housing between said pistons.

3. A device as defined in claim 1 wherein said piston means comprise a set of axially spaced pistons supported within said control housing for axial movement, and said valve includes a disk-like valve member rotatably supported by said housing between said pistons and defining a circumferentially extending tapered flow passage for selecting the flow rate of the hydraulic fluid between said pistons and through said passage in response to rotation of said valve member.

4. A device as defined in claim 1 and including a set of gear sections connecting said arms together adjacent said hub member, said arms are supported by said hub member for pivotal movement on two parallel spaced axes, and said link member is connected to said hub member eccentrically of said two axes.

5. A device as defined in claim 1 wherein said piston means comprise a set of axially spaced pistons supported within said housing for axial movement, and means including a plurality of independently adjustable said control valves rotatably supported by said housing between said pistons for controlling the displacement of hydraulic fluid within said housing.

6. An articulated limb resistance device comprising a hub, a set of arms projecting outwardly from said hub, pivot means connecting said arms to said hub for pivotal movement of said arms relative to each other, attachment members for releasably attaching said arms to a person's limb on opposite sides of a joint within the limb, a hydraulic resistance unit including a tubular housing mounted on one of said arms, a set of axially spaced pistons supported within said housing for axial movement, an actuator including a link member connecting said pistons to each other and to said hub eccentrically of the pivot axis of said one arm, and means including at least one adjustable control member connected to change the flow of hydraulic fluid within said housing between said pistons for adjustably selecting the resistance to pivotal movement of said arms.

7. A brace as defined in claim 6 wherein said control member comprises at least one disk-like valve member rotatably supported by said housing between said pistons and defining a circumferentially extending tapered flow passage for selecting the flow rate of the hydraulic fluid between said pistons and through said passage.

8. An articulated limb resistance device comprising a hub, a set of arms projecting outwardly from said hub, pivot means connecting said arms to said hub for pivotal movement of said arms relative to each other, attachment members for releasably attaching said arms to a person's limb on opposite sides of a joint within the limb, a hydraulic resistance unit mounted on one of said arms and including an actuator connected to resist pivotal movement of said arms, said resistance unit including a set of adjustable valves, and adjustable control members connected to said valves to change the resistance to movement of said actuator and said arms and to provide for independent adjustment of the resistance to flexion and extension of said device.

9. A brace as defined in claim 8 wherein said hydraulic resistance unit includes a tubular housing mounted on one of said arms, said actuator comprises a set of axially spaced pistons supported within said housing for axial movement, a shaft connecting said pistons to each other, and a link member connecting said pistons to said hub eccentrically of the pivot axis of said one arm.

10. An articulated limb brace comprising a hub, a set of arms projecting outwardly from said hub, pivot means connecting said arms to said hub for pivotal movement of said arms relative to each other, attachment members for releasably attaching said arms to a person's limb on opposite sides of a joint within the limb, a hydraulic resistance unit including an actuator connected to displace hydraulic fluid within said unit in response to pivotal movement of said arms, a plurality of adjustable valves connected for adjustably controlling tile flow rate of hydraulic fluid displaced within said unit in response to movement of said arms for independently selecting the resistance to flexion and extension of said arms and the limb, and said valves including an on/off valve for selecting between resistance to pivotal movement of said arms and substantially no resistance.

11. A brace as defined in claim 10 wherein said hydraulic resistance unit includes a tubular housing mounted on one of said arms, said actuator comprises a set of axially spaced pistons supported within said housing for axial movement, a shaft connecting said pistons to each other, a link member connecting said pistons to said hub eccentrically of the pivot axis of said one arm, and each of said valves includes a rotatable disk-like valve member positioned within said housing between said pistons.

12. A brace as defined in claim 10 wherein said hydraulic resistance unit includes a tubular housing mounted on one of said arms, said actuator comprises a set of axially spaced pistons supported within said housing for axial movement, and each said valve includes a disk-like valve member rotatably supported by said housing between said pistons and having a radial face defining a circumferentially extending tapered flow passage for selecting the flow rate of the hydraulic fluid between said pistons and through said passage in response to rotation of said valve member.

13. A brace as defined in claim 12 and including a link member connecting said pistons to said hub eccentrically of the pivot axis of each said arm.

14. A brace as defined in claim 10 wherein said attachment members comprises a set of pads connected to at least one of said arms, a set of flexible straps connected to said set of pads, and said straps including means for clamping said set of pads tighter on said one arm in response to tightening of said straps around the limb.

* * * * *